United States Patent [19]
Silver et al.

[11] Patent Number: 5,336,198
[45] Date of Patent: Aug. 9, 1994

[54] HYPODERMIC SYRINGE WITH NEEDLE RETRACTION FEATURE

[75] Inventors: Jules Silver, Boca Raton, Fla.; Louis C. Ziegler, Englewood Cliffs, N.J.

[73] Assignee: Innova Development Corp., Boca Raton, Fla.

[21] Appl. No.: 11,942

[22] Filed: Feb. 1, 1993

[51] Int. Cl.⁵ .......................... A61M 5/32; A61M 5/00
[52] U.S. Cl. ...................................... 604/195; 604/110
[58] Field of Search .............. 604/110, 192, 195, 240, 604/263

[56] References Cited

U.S. PATENT DOCUMENTS

| | | | |
|---|---|---|---|
| 4,507,117 | 3/1985 | Vining et al. | 604/196 |
| 4,675,005 | 6/1987 | Deluccia | 604/110 |
| 4,692,156 | 9/1987 | Haller | 604/195 |
| 4,710,170 | 12/1987 | Haber et al. | 604/110 |
| 4,747,830 | 5/1988 | Gloyer et al. | 604/110 |
| 4,770,655 | 9/1988 | Haber et al. | 604/110 |
| 4,790,822 | 12/1988 | Haining | 604/110 |
| 4,790,822 | 12/1988 | Haining | 604/110 |
| 4,804,370 | 2/1989 | Haber et al. | 604/195 |
| 4,826,484 | 5/1989 | Haber et al. | 604/110 |
| 4,883,471 | 11/1989 | Bragenetz et al. | 604/195 |
| 4,909,794 | 3/1990 | Haber et al. | 604/195 |
| 4,919,652 | 3/1990 | Alter et al. | 604/110 |
| 4,944,723 | 7/1990 | Haber et al. | 604/110 |
| 4,950,241 | 8/1990 | Ranford | 604/110 |
| 4,950,251 | 8/1990 | Haining | 604/195 |
| 4,978,340 | 12/1990 | Terrill et al. | 604/195 |
| 4,978,343 | 12/1990 | Dysarz et al. | 604/195 |
| 4,986,813 | 1/1991 | Blake, III et al. | 604/110 |
| 4,994,034 | 2/1991 | Botich et al. | 604/110 |
| 4,995,874 | 2/1991 | Strickland | 604/195 |
| 5,000,736 | 3/1991 | Kaufhold, Jr. et al. | 604/110 |
| 5,019,043 | 5/1991 | Segui Pastor et al. | 604/110 |
| 5,019,044 | 5/1991 | Tsao | 604/110 |
| 5,030,208 | 7/1991 | Novacek et al. | 604/195 |
| 5,047,016 | 9/1991 | Dolgin et al. | 604/110 |
| 5,085,638 | 2/1992 | Farbstein et al. | 604/110 |
| 5,098,390 | 3/1992 | Wallingford | 604/195 |
| 5,098,402 | 3/1992 | Davis | 604/195 |
| 5,104,378 | 4/1992 | Haber et al. | 604/110 |
| 5,125,898 | 6/1992 | Kaufhold, Jr. et al. | 604/110 |
| 5,152,750 | 10/1992 | Haining | 604/195 |
| 5,171,300 | 12/1992 | Blake, III et al. | 604/110 |
| 5,176,640 | 1/1993 | Nacci et al. | 604/110 |
| 5,188,599 | 2/1993 | Botich et al. | 604/110 |
| 5,190,526 | 3/1993 | Murray et al. | 604/110 |
| 5,205,823 | 4/1993 | Zdeb | 604/195 |
| 5,205,824 | 4/1993 | Mazur | 604/195 |
| 5,215,533 | 6/1993 | Robb | 604/195 |
| 5,232,458 | 8/1993 | Chen | 604/195 |
| 5,242,400 | 9/1993 | Blake, III et al. | 604/110 |
| 5,273,543 | 12/1993 | Bell et al. | 604/195 |

FOREIGN PATENT DOCUMENTS 0347742 12/1989 European Pat. Off. .......... 604/110

Primary Examiner—C. Fred Rosenbaum
Assistant Examiner—Frank Wilkens
Attorney, Agent, or Firm—Harry W. Barron

[57] ABSTRACT

An improved hypodermic syringe includes a needle retraction feature permitting the needle to be fully retracted into the cylindrical cavity of the syringe barrel following the injection of medicine into a patient. The needle is held on the distal end of the barrel by means of an attachment hub, which includes an internal abutment surface to prevent outward movement of the needle. Inward movement of the needle is prevented by an expandable restriction of a distal barrel opening, extending between the cylindrical cavity and the distal end of the barrel. The needle is part of a subassembly including a flange held between this internal abutment surface and this expandable restriction. The distal end of the plunger is fitted with a needle extractor, which moves into the distal barrel opening as the plunger is pushed fully into the cylindrical cavity. The needle extractor grips the proximal end of the needle subassembly and expands the expandable restriction so that the needle subassembly, with its flange, is pulled into the cylindrical cavity as the plunger is pulled outward. The needle extractor may be elastically mounted on the plunger, pointing at an acute angle with the axis of the cylindrical cavity, so that the needle is rotated to point toward the side of the barrel as it is pulled fully within the cavity.

60 Claims, 3 Drawing Sheets

HYPODERMIC SYRINGE WITH NEEDLE RETRACTION FEATURE

BACKGROUND OF THE INVENTION

Field of the Invention

This invention relates to a hypodermic syringe, and more particularly, to a disposable hypodermic syringe having a needle which may be retracted into the cylindrical cavity of the barrel following use.

Background Information

A typical hypodermic syringe includes a transparent cylindrical barrel, generally open at a proximal end, a plunger assembly movable within the barrel to dispense medication, and a needle assembly removably attached to the barrel at a distal end by means of a locking mechanism, such as Luer lock. During usage, medication is sealed within open side of the barrel by means of a rubber piston slipped over the distal end of the plunger. At the distal end of the syringe, sealing is accomplished through a sealant, such as an epoxy resin, extending between the outer surface of the needle and the lock hub carrying the needle. This sealant, and the locking mechanism fastening the needle assembly to the barrel, are also used to transmit the force, which may be as high as several pounds, required to insert the needle into the patient's body and to remove the needle after the injection process is complete.

The applications of hypodermic syringes within a health care facility require the availability of syringes varying particularly in needle length and diameter, and in the dosage capacity of the barrel. To satisfy this need, needles and the remaining portions of syringes are made commercially available both as assembled units, and as separate units allowing the attachment of a selected one of the various needle assemblies to a selected one of various barrels. The Luer lock fittings used to fasten the needle to the barrel form a basis for common, interchangeable parts.

It is thus desirable that any improved design for hypodermic syringes should include the capability of switching needles among the syringes. It is even more desirable that any improved design for hypodermic syringes should be capable of using standard needle assemblies, and that the new needle assemblies should be usable in standard syringe barrels.

Modern medical practice dictates that, in order to elimihate a possible source of contagious disease, hypodermic syringes are used only once. There is a growing concern, even when syringes are discarded immediately after use, that health care workers may be accidently stuck by a hypodermic needle which has been used in the treatment of a patient having a serious communicable disease, such as AIDS or hepatitis. Used hypodermic needles have become an especially dangerous form of waste material, posing a danger to anyone handling trash from a health care facility and to anyone who might come into contact with such material after it has been dumped, and requiring special puncture resistant containers for disposal.

Another problem commonly associated with discarded hypodermic syringes is their potential use by drug abusers, who sometimes search waste material from health facilities for such devices. This practice obviously carries a significant risk of infection to these drug users and to others they may subsequently contact.

Conventional hypodermic syringes included an inward extending ring near the proximal opening of the barrel, which forms a stop, preventing the inadvertent removal of the plunger from the barrel. However, this ring is generally not rigid enough to prevent the deliberate, surreptitious removal of the plunger, as by a drug abuser.

Description of the Prior Art

One prior art solution to the aforementioned problems has been to enclose the needle in a sheath manually slipped over the needle end before and after use of the syringe. However, this technique still exposes health workers to the risk of being stuck with an infected needle as the sheath is slipped on, particularly when the needle is not properly aligned with the sheath opening. Furthermore, this technique does nothing to render the syringe useless to a drug abuser.

Another prior art solution to the aforementioned problems is breaking the needle from the syringe once it is used. While this procedure is followed in a number of health care facilities, there are still several disadvantages to this procedure. First, the broken needles are not necessarily enclosed in a way permitting their subsequent safe handling, and second, the additional handling of used needles by health care workers in the process of breaking the needles may increase the risk of their being accidently stuck by an infected needle.

One attractive solution to the aforementioned problems is in providing a syringe/needle assembly in which the needle may be retracted into the barrel of the syringe after use, so that the needle is held in an envelope formed by the barrel during disposal. The patent literature includes descriptions of devices of a first general type, in which a needle is fastened to a needle carrier which travels axially within the barrel. In its distal position, the carrier holds the needle ready for use at the distal end of the barrel. After the plunger assembly is moved to the distal end of the barrel, after dispensing the desired medication, the plunger assembly engages and locks onto the needle carrier. When the plunger assembly is subsequently withdrawn and returned to the proximal end of its travel, the needle is carried with the plunger until it is completely enclosed within the barrel. At this point, the syringe ready for proper and safe disposal. Examples of syringes of this type are found in U.S. Pat. No. 4,710,170, issued to Haber et al on Dec. 1, 1987; in U.S. Pat. No. 4,790,822, issued to Haining on Dec. 13, 1988; and in U.S. Pat. No. 4,883,471, issued to Braginetz et al on Nov. 28, 1989.

In the prior art devices, the needle is fastened to the needle carrier by conventional means. For example, needle may be fastened to a Luer lock hub, which, in turn, is screwed onto a threaded hole forming internal surfaces in the needle carrier. Thus, syringes of this kind have the advantage of being capable of using standard needle assemblies of the types widely available for syringes not incorporating the safety feature of needle retraction. If the syringe is provided with its needle carrier at the distal position, an interchangeable needle may be screwed into the syringe from the distal end, in the conventional manner. However, the barrels of syringes of this type, of necessity, have relatively large openings at their distal ends, to accommodate the motion of the needle, together with a portion of the needle carrier as it is retracted into the barrel. This large opening, in turn, significantly increases the complexity and cost of the device by requiring fluid tight sealing around the outside of the needle carrier, so that medicine can be dispensed through the needle without leakage out of the distal end of the syringe.

Furthermore, the needle carrier of the prior art devices occupies a significant portion of the axial length of the barrel. The conservation of distance along this length is especially important in a syringe having a retractable needle because the space is needed for storage of the needle after use. Conventional syringes are built to particular sizes for convenient handling and use, as well as for various barrel capacities for medication. For example, the barrels of typical syringes having either three cubic centimeter and five cubic centimeter capacities are about 2.5 inches in length, with the difference in capacity being accomplished by varying the diameter. A typical long needle extends 1.5 inches from the end of the Luer hub to which it is attached. Including this hub, the length of the needle assembly is about 2.125 inches. Thus, the use of a needle carrier of the prior art requires lengthening the barrel beyond the length necessary for handling and capacity, thereby decreasing the ease and familiarity with which the syringe is handled and further increasing its costs of manufacture and distribution.

The device of U.S. Pat. No. 4,883,471 to Braginetz et al mounts the needle carrier in a second piston. After the medication is dispensed, vent ports are opened by rotating a cap at the distal end of the syringe, so that the atmosphere is allowed to enter the syringe at the distal end of this second piston. The retraction of the piston, with the needle, is then accomplished by the differential pressure established as the plunger is withdrawn. However, rotating the cap in this way presents the health care worker with the inconvenience of an extra step in the process.

The patent literature also describes devices of a second general type, in which the needle assembly is loaded into the syringe barrel from inside the barrel, to stick outward through a relatively small opening in the distal end of the barrel. After the injection of medicine by means of the plunger assembly, the needle assembly is attached to the distal end of the plunger assembly to be retracted into the syringe barrel as the plunger assembly is pulled back toward the proximal end of the barrel.

While syringes of this type address the concerns expressed above relative to the use of a separate needle carrier, they lack the important ability to use conventional needle assemblies, which are adapted to be screwed into place using Luer couplings from outside the distal end of the barrel. In addition, if interchangeable needles are to be used in any way on the syringes, they must be attached by relatively difficult or complex means within the barrels. Further, by changing a needle through the barrel, the sterility of the barrel can be violated.

Some devices of this second general type, in which the needle is loaded from inside the barrel, include couplings between the needle assemblies and the distal ends of the barrels, which are connected and disconnected by the rotation of the needle assembly within the barrel, being described, for example, in U.S. Pat. No. 4,507,117, issued to Vining et al on Mar. 26, 1985; in U.S. Pat. No. 4,675,005, issued to DeLuccia on Jun. 23, 1987; in U.S. Pat. No. 4,747,830, issued to Gloyer et al on May 31, 1988; in U.S. Pat. No. 4,919,652, issued to Alter et al on Apr. 24, 1990; and in U.S. Pat. No. 4,986,813, issued to Blake III et al on Jan. 22, 1991. While DeLuccia, Alter, and Blake III teach the use of threaded screw connections, Vining and Gloyer uses quick release, quarter turn types of connection. Vining also describes means for providing the syringe, before use, with the needle retracted for safe handling. A disadvantage of these syringes is the additional requirement that the plunger must be twisted after an injection is given, before disposal of the syringe with the needle assembly in a retracted position. This twisting is needed to engage the needle assembly to the plunger assembly, and to disengage the needle assembly from the distal end of the barrel. However, this requirement places a burden on health care workers in an emergency situation, and can be expected to result in a failure to properly retract needles in some units before disposal.

Other devices of this in which the needle is loaded through the barrel interior include means for engaging the proximal end of the needle assembly with a mechanism extending from the distal end of the plunger assembly as the plunger mechanism reaches the distal end of its travel in dispensing medicine through the needle. Such devices are described, for example, in one of the embodiments of U.S. Pat. No. 4,675,005 to DeLuccia; in one of the embodiments of U.S. Pat. No. 4,692,156 to Haller; and in U.S. Pat. No. 4,804,370, issued to Haber et al on Feb. 14, 1989. In this Haber device, the needle extends outward through a small hole at the distal tip of the syringe barrel. The proximal end of the needle is provided with a flange, and the plunger assembly is provided with a needle capturing receptacle which engages this flange as the plunger assembly is moved to the distal end of the barrel, so that the needle is subsequently retracted into the barrel as the plunger assembly is withdrawn.

While such devices are operable without requiring the additional step of twisting the plunger after medicine is dispensed, they are still inconvenient to use, when compared to conventional syringes, because they do not accept conventional needle assemblies, and because, if it is necessary to install any type of needle assembly, the installation procedure is relatively complex and would violate the integrity of the sterility.

An important consideration in the design of a hypodermic syringe is the ability of the device to transmit axial forces to the needle from the barrel and plunger. Forces as high as several pounds may be required, both to insert the needle into the patient, and to withdraw the needle from the patient during the process of giving an injection. If the needle is to be retracted into the barrel of the syringe, means must be provided to prevent this retraction during the insertion of the needle into the patient, due to the necessary application of force to the needle as it is inserted.

In the devices having needle assemblies connected to the barrels with screw threads or quarter turn fasteners, to be disconnected by rotation of the plunger after the medication is dispensed, these fasteners prevent premature retraction of the needle. These devices are shown, for example, in U.S. Pat. Nos. 4,507,117, 4,675,005, 4,747,830, 4,919,652, and 4,986,813. While this method of holding the needle in place during injection is quite effective, the disadvantages of requiring the performance of the additional manual rotation step and nonstandard components remains.

In those devices having means for engaging the proximal end of the needle assembly with a mechanism extending from the distal end of the plunger assembly, the connection between the needle and the barrel must be strong enough to hold the needle in place as it is inserted into the patient. Further, the needle must subsequently be pulled directly out of this connection for retraction. Both of these actions are accomplished by applying an axial force to the needle. In the devices of U.S. Pat. No. 4,692,156 to Haller, the needle is mounted in an aperture within a deformable tapered mounting post, which deforms to slide through a passage in the barrel during retraction. In other devices, as shown, for example in U.S. Pat. Nos. 4,804,370 and 4,826,484 to Haber et al., the needle is retained by a tight fit within a distal hole of the barrel. This means that, for reliable operation, the force which must be applied for needle retraction, to overcome the attachment between the needle and the barrel, must be greater than the highest force expected during the insertion of the needle into the patient, together with a safety factor applied to cover variations in the process of manufacturing the syringe. If the needle is to be retracted during withdrawal from the patient, this force must be even higher. The requirement to apply such a large force places a significant burden on health care personnel and creates a potential danger to the patient.

The device described in U.S. Pat. No. 4,710,170 to Haber et al includes a needle carrier which is held in place within the barrel by means of a quick release fastener. After the dispensing of medication is completed, the plunger is manually rotated to release the carrier from engagement with the barrel. Thus, a requirement to perform an additional step is placed on health care personnel.

The device described in U.S. Pat. No. 4,790,822 to Haining includes a needle carrier which is held in place at the distal end of the barrel by opposing shoulders extending inward from the interior of the barrel. As the plunger is moved to the distal end of the barrel, a piston at the distal end of the plunger forces these shoulders apart, releasing the carrier to return with the plunger.

The patent literature also describes apparatus for causing the needle to be rotated transversely, about its attachment to the plunger as it is retracted into the barrel, to point toward a side of the barrel. This is done to prevent accidental or deliberate extension of the needle through the hole in the distal end of the barrel, by means of pushing the plunger inward. In other words, this feature provides further safety for health care and trash disposal workers, and goes another step toward preventing the subsequent use of the syringe by drug abusers. For example, U.S. Pat. No. 4,804,370, issued to Haber et al on Feb. 14, 1989, describes needle capturing receptacle with legs, for capturing a flange at the proximal end of the needle. Two of the legs are shorter than the others, so the needle is rotated transversely as it is retracted. As described in U.S. Pat. No. 4,986,813 to Blake III et al, a syringe includes a fitting fastening the needle assembly to the distal end of the plunger for retraction with a slot, extending inward from one side of the fitting, which is allowed to expand as the needle is fully retracted, throwing the needle out of alignment with the longitudinal axis of the plunger.

Blake III also describes the use of stopping surfaces extending into the barrel near its proximal end, angled to prevent removal of the plunger from the barrel, while allowing its assembly into the barrel as the syringe is fabricated. Such surfaces make it particularly difficult for a drug user to take the syringe apart to make it again operable or to retrieve the needle.

Thus, while the feature of needle retraction can be accomplished in a number of ways, the methods proposed in the prior art for providing this feature all have various disadvantages. What is needed is apparatus for providing needle retraction without substantially increasing the size or length of the syringe, as required when a separate needle carrier is employed, and without requiring the performance of an additional step, such as the rotation of the plunger, by health care personnel. Since health care facilities must carry a relatively large inventory of different sizes and types of syringes and needles, it is desirable that an improved syringe should accept the removal and attachment of needles in the standard way, from outside the distal end of the barrel. It is further desirable that the needle be releasibly held in place by positive means, such as a latch or movable abutting surface, rather than by reliance on a tight fit. Also, since conventional hypodermic syringes are low cost items used in large quantities by health care facilities, it is particularly desirable that the feature of needle retraction should be provided by a mechanism which is inherently simple and low in manufacturing cost. In particular, any improved syringe ideally will use existing syringe parts or slight modified parts so that existing mold tooling can be used.

SUMMARY OF THE INVENTION

In accordance with one aspect of the invention, there is provided a hypodermic syringe including a container for ejecting fluid having an internal cavity between a fluid ejecting end thereof and a proximal end thereof. The container also has a piston assembly having a seal end movable from the proximal end to the fluid ejecting end to eject fluid and retractable towards the proximal end. The syringe further includes a needle attachment assembly affixed to the fluid ejecting end of the container, the needle attachment assembly having a hollow first column with an opening extending therethrough in fluid communication with the cavity. The column is tapered inward at a distal end thereof and has a plurality of slits from the distal end thereof towards the container separating a plurality of segments at the distal end. In addition, the syringe includes a needle subassembly, including a needle with hole extending axially therethrough, and a needle flange affixed remote from one end of the needle. A second hollow column extends from the flange towards the one end and is sized to fit within the first column opening such that the end of the segments are juxtaposed to one surface of the flange. The needle subassembly further includes means juxtaposed to the other side of the flange for holding the needle subassembly on the attachment assembly column. Finally, the syringe includes needle extractor means, including a third hollow column affixed to the seal end of the piston assembly. The third column is sized such that the exterior thereof enters the first column and separates the segments so that the ends thereof are spaced from the one surface of the flange. The third column further is sized such that the interior thereof grabs the second column and the needle assembly, including the flange is retracted through the first column upon retraction of the piston assembly.

BRIEF DESCRIPTION OF THE DRAWINGS

Preferred embodiments of the subject invention are hereafter described with specific reference being made to the following Figures, in which.

DETAILED DESCRIPTION

Figure 1:
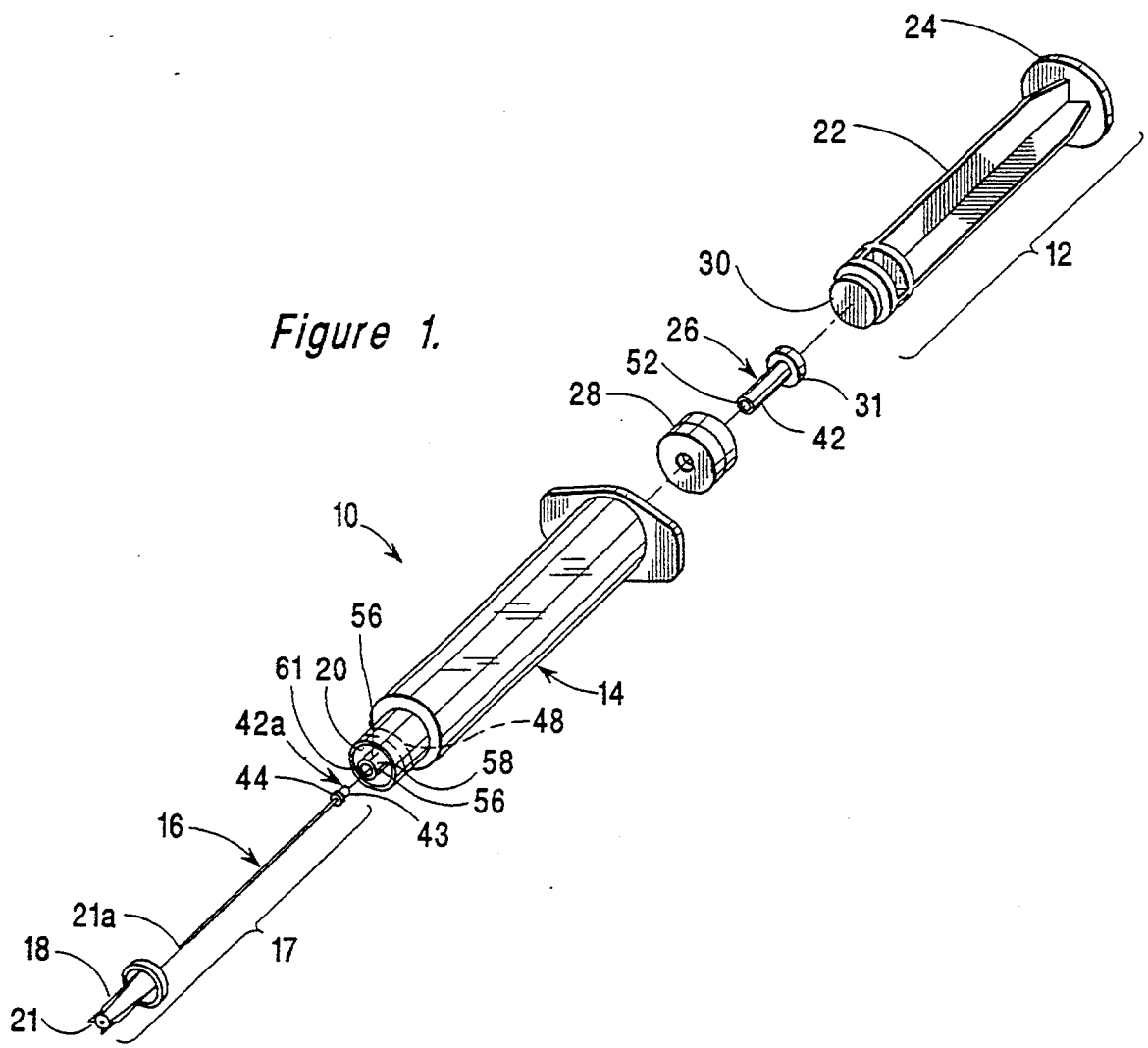
FIG. 1 is an exploded isometric view of a hypodermic syringe built in accordance with the present invention.

Referring first to FIG. 1, an improved hypodermic syringe 10 of the subject invention includes a plunger assembly 12 slidable within a barrel 14 to dispense medication by means of a hole extending through a needle 16 within a needle assembly 17. This needle assembly 17 includes needle 16 and a Luer hub 18 by which the needle is removably attached to threaded hole 20 at the distal end of barrel 14. Luer hub 18 includes longitudinally extending external flutes 21, which aid in gripping needle assembly 17 for rotation as required to engage or disengage the threaded Luer connection. Needle assembly 17 may also be provided with a sheath (not shown), extending around the needle 16 and attachable to hub 18 to protect health care personnel from contact the sharp distal point 21a of the needle. Flutes 21 may also engage internal grooves extending longitudinally within the sheath to permit the rotation of the needle assembly 17 without removing the sheath. Plunger assembly 12 includes an elongated slide 22 having gripping means 24 at its proximal end, an inward extending needle extractor 26, and an elastomeric piston 28 which extends over a disk shaped distal end portion 30 of slide 22, and around a flange 31 of extractor 26.

Figure 2:
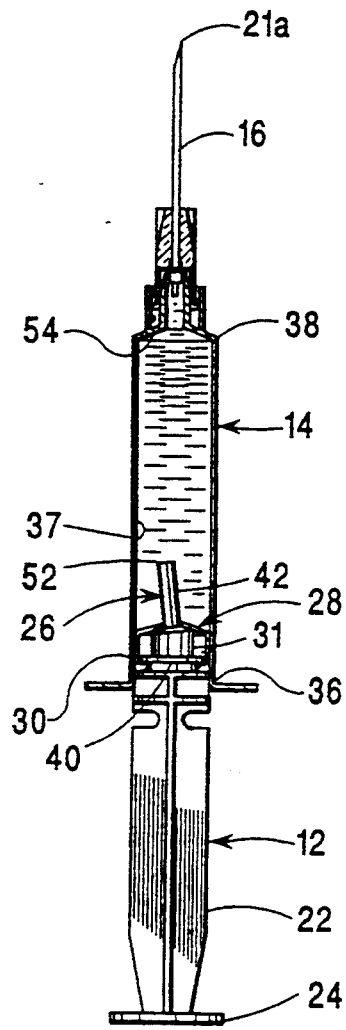
FIG. 2 is a longitudinal elevation of the syringe of FIG. 1, being shown as ready to dispense medication.

FIG. 2 shows syringe 10 as ready to dispense medication 34 through needle 16. This medication 34 may have been drawn through needle 16 from a vial, not shown, as plunger assembly 12 was moved to the position shown near the proximal end 36 of barrel 14. Alternatively, the medication 34 may have been supplied to a health care facility as part of the syringe package. Elastomeric piston 28 forms a seal around the internal cylindrical surface 37 of barrel 14, so that pressure may be built up within the cylinder interior of barrel 14 by sliding plunger assembly 12 toward distal end 38, as required to dispense the medication 34 through needle 16, without substantial leakage of the medication 34 past piston 28.

Figure 4:
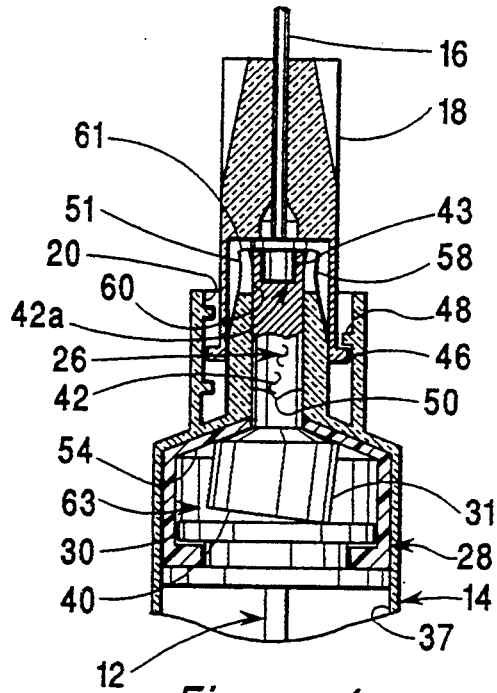
FIG. 4 is a cross-sectional elevation similar to FIG. 3, shown with the needle engaged for retraction into a barrel of the syringe.

A more detailed view of the relationships among slide 22, elastomeric piston 28, and needle extractor 26 is also provided in the cross-sectional view of FIG. 4. Elastomeric piston 28 is essentially a hollow cylindrical structure having a large hole in one end, through which distal end portion 30 of slide 12 is inserted, and a smaller hole in the opposite end, through which flange 31 of needle extractor 26 is inserted. The elastic properties of piston 28 produce a clamping action to hold flange 31 against end portion 30. Alternatively, needle extractor 26 may be secured to end portion 30 by a suitable adhesive or may be molded as a part of the slide 22 and end portion 30 assembly. Since the proximal end surface 40 of flange 31 is slanted relative to the axis of hub portion 42 of extractor 26, hub portion 42 is slanted, at an acute angle to the longitudinal axis of barrel 14, when flange 31 and end portion 30 are held together in this way.

Figure 3:
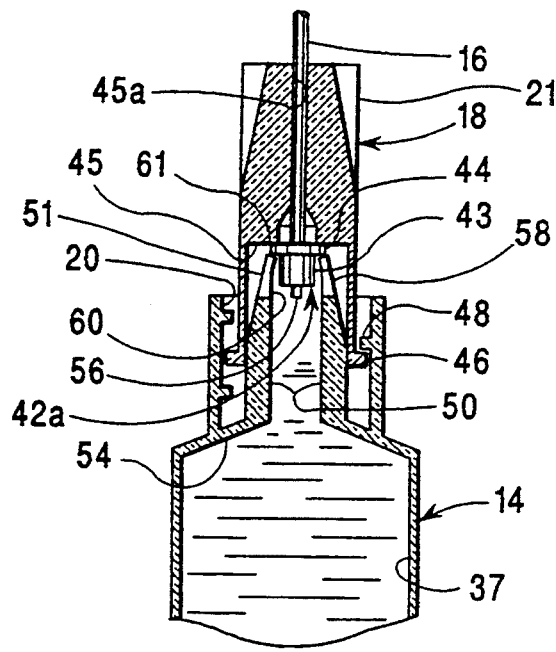
FIG. 3 is a fractional longitudinal cross-sectional elevation of the needle attachment portion of the syringe of FIG. 1.

The manner by which needle 16 is attached to barrel 14 is shown particularly in FIG. 3. A metal, or other hard material, collar 42a, including a hub 43 and a flange 44, is fastened to a proximal end of needle 16, preferably by a swaging procedure or an adhesive, to form a needle subassembly. Needle assembly 17 is formed when needle 16 is subsequently inserted through a needle receiving hole 45a in Luer hub 18, being pushed through this hole 45a until needle 16 extends through hub 18, with a distal side of flange 44 against an adjacent abutment surface 45 of the hub.

A sealant is preferably added to the annular space between needle 16 and the internal surface of needle receiving hole 45a. The need for this form of sealing exists because, while it is neither necessary nor desirable to produce a tight fit between needle 16 and hub 18, it is necessary to establish a partial vacuum within syringe 10 as plunger assembly 12 is pulled outward to fill the syringe with medication 34. Further, necessary to establish hydraulic pressure within syringe 10 as plunger 12 is subsequently pushed inward to inject the medication 34 into a patient. Thus, there is a need to prevent the inward leakage of air, or the outward leakage of medication, through the space between needle 16 and hub 18. However, it is necessary that the sealing agent does not permanently bond to the needle.

Several different types of sealants may be used to seal needle 16 and hole 45a. For example, a heavy grease, such as a petroleum jelly may be used for the sealant, as can a number of room temperature vulcanizing (RTV) silicone adhesives, or yieldable medical adhesives, such as the product available as Dymax Light Weld #190-M.

Flange 44 includes an annular shoulder preventing outward movement of needle 16 by contact with an adjacent internal abutment surface 45 of Luer hub 18. Luer hub 18 includes, at its proximal end, a conventional thread engaging flange 46, shaped as a disk with truncated sides, which engages an internal thread 48 within threaded hole 20 of barrel 14. In this way, needle assembly 17 is removably fastened to barrel 14. A number of different needle assemblies can be provided for interchangeable attachment in this manner, with such needle assemblies varying, for example, in the length and diameter of the needle.

Thus, while the needle retraction feature is provided by means which will be explained, the attachment of the needle to the syringe barrel is achieved by conventional means, through the use of a Luer connection allowing attachment from outside the distal end of the syringe barrel. In fact, conventional needle assemblies, without provision for needle retraction, can be attached through this conventional connection to syringe barrel 14 built in accordance with the present invention, and needle assemblies 17 built in accordance with this invention can be attached to conventional syringe barrels. If parts made in accordance with this invention are assembled with conventional parts in either of these ways, the needle retraction feature will not be operative, but the syringes can still be used and disposed in conventional ways. This is a particular advantage to a health care facility, with an inventory of conventional needles and syringes, in the process of converting to the use of syringes having the needle retraction feature.

This needle attachment arrangement of the subject invention offers particular advantages, of ease of use and interchangeability with conventional parts, over the arrangements shown, for example, in U.S. Pat. No. 4,826,484 to Haber et al, in which a needle must be pressed into a tight fitting hole from inside the barrel cavity. This needle attachment arrangement of the subject invention offers advantages over the arrangements of, for example, U.S. Pat. Nos. 4,675,005 to DeLuccia, 4,747,830 to Gloyer et al, 4,919,652 to Alter et al, and 4,986,813 to Blake III et al, which require that the needle assembly must be screwed into a threaded hole, or into a quick release fastener, within the distal end of the barrel, from inside the barrel cavity.

During the process of handling syringe 10 before an injection is given and during the process of dispensing medication 34 by means of injection, needle 16 is held by the distal end of barrel 14, since flange 44 cannot pass through the smaller diameter distal opening of channel 50 provided at the distal end of coupling 51 of barrel 14. Thus, flange 44 provides an annular shoulder on each side, serving in the transmission of any thrust forces in either direction, which may occur at the needle during the injection process.

Referring again to FIG. 2, an injection is given to the patient in the conventional way, by moving plunger assembly 12 through the cylindrical interior of barrel 14. As plunger assembly 12 nears the distal end of barrel 14, distal tip 52 of the hub 42 portion of needle extractor 26 contacts funnel shaped internal surface 54 of barrel 14. As noted above, needle extractor 26 is maintained out of alignment with the axis of channel 50 by means of the engagement between slider end portion 30 and extractor flange 31. However, the angle of funnel shaped surface 54 is sufficient to ensure that tip 52 is guided into alignment with channel 50 with continued motion of plunger assembly 12 into barrel 14, when tip 52 in contact with surface 54.

Referring again to FIG. 3, the distal end of coupling 51 is slanted slightly inward and has a series of inward extending slots 56 at a narrowed portion 60 of channel 50, separating the distal end of coupling 51 into plural segments 58. When extractor tip 52 is brought into engagement with needle hub 43, slots 56 are sized to receive hub 42 of extractor 26 and permit the expansion of the distal end of coupling 51 by the flexure of the segments 58 formed between slots 56. The expansion of segments 58 only occurs as extractor tip 52 is brought into the narrowed portion 60 at the extreme distal end of channel 50.

Thus, thrust forces required for the insertion of a portion of needle 16 into the patient are provided through the abutment of needle flange 44 and the ends 61 of segments 58 prior to the separation of segments 58. This structure provides a particular advantage over the prior art, for example, in U.S. Pat. No. 4,826,484 to Haber et al, which requires that the thrust forces to be provided through a tight fit between the needle and a distal hole in the barrel, which fit is much more prone to failure than the abutting structure of ends 61 against flange 44. With the structure of the present invention, sufficient force to deflect segments 58 outward is applied at the very end of the inward movement of plunger assembly 12, long after the needle is fully inserted in the patient and at the time the medicine is dispensed.

Further, the disengagement of the abutting structure of ends 61 against flange 44 is accomplished by deflecting segments 58 arranged to extend as cantilever springs. This structure has the significant advantage of requiring very low deflection forces compared to the those required by the structure of the prior art. For example, in U.S. Pat. No. 4,790,822 to Haining, the abutting surfaces are provided as parts of shoulders extending inward from the wall of the syringe barrel, so that this wall must be deflected outward around all sides of the shoulders before the needle can be retracted with a needle carrier.

As shown in FIG. 4, when the motion of plunger assembly 12 toward the distal end of barrel 14 has been completed, distal tip 52 of needle extractor 26 has moved through channel 50 to engage needle hub 43 for the retraction of needle 16. At this position, a wedge shaped gap 63 exists between proximal surface 40 of flange 31 and distal end 36 of slide 22 resulting from needle extractor 26 being guided into channel 50. Tip 52 has a tubular shape, which tightly holds needle hub 43. The expansion of coupling tip 58 with the insertion of extractor tip 52 enlarges the narrowed opening 60 of channel 50 to clear the diameter of flange 44, so that needle 16 may be retracted into barrel 14 with the subsequent pulling of plunger assembly 12 towards proximal end 36 of the barrel using gripping means 24.

Figure 6:
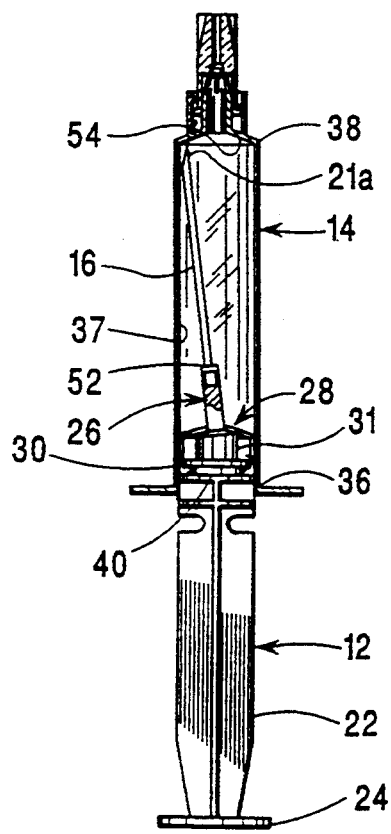
FIG. 6 is a cross-sectional elevation similar to FIG. 2, shown with the needle fully retracted after dispensing medication.

As shown in FIGS. 3 and 4, as needle 16 is about to be retracted from the patient, it is held by flange 44 abutting against abutment surface 45 of Luer hub 18. Thus, as cylinder 14 is pulled rearward, needle 16 moves with cylinder 14 due to the abutment of flange 44 against Luer hub 18. With this structure, the needle retraction feature is included in syringe 10 without significantly, if at all, increasing the length of the parts subsequently moved into the interior of barrel 14, as seen in FIG. 6. Thus, it is not necessary to increase the length of barrel 14, beyond the normal length of barrel 14, which already is sufficient to hold needle 16 itself. A syringe with the size and length of a conventional syringe can be thus provided with the needle retraction feature using most existing parts. In this regard, a particular advantage is gained relative to the use of a separate needle carrier, slidably mounted to move in a syringe barrel cylinder, as shown, for example in U.S. Pat. Nos. 4,710,170 to Haber et al, 4,790,822 to Haining, and 4,883,471 to Braginetz et al. Further, the needle holding structure of the present invention makes it unnecessary to seal around the large diameter of a separate needle carrier.

Figure 5:
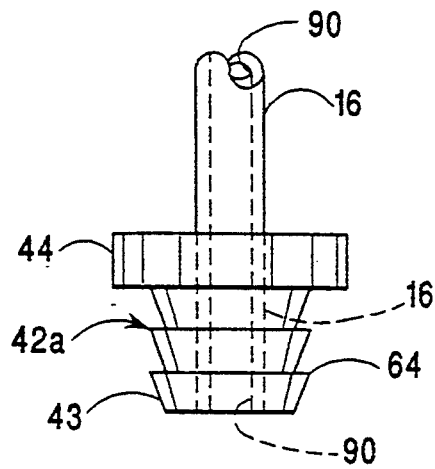
FIG. 5 is an elevational view of the proximal end of a needle of the syringe of FIG. 1.

It is desirable to remove needle 16 from the patient by pulling plunger assembly 12 while pushing cylinder assembly 14 in order to maintain the distal end of cylinder assembly against the skin of the patient as needle 16 is drawn into cylinder 14. Referring to FIG. 5, needle retraction using plunger assembly 12 may be accomplished by providing needle hub 43 with one or more ridges 64 to increase the thrust force which can be applied to extract needle 16 without breaking the bond between retraction assembly 26 and needle 16. In FIG. 5, needle 16 is shown extending through an opening 88 in flange 44 and hub 43 permitting fluid communication through the opening 90 in needle 16. Alternatively, flange 44 and hub 43 may be integrally formed as a part of needle 16. Further, the internal surface of extractor hub 42 may also be provided with ridges, or reliance can be made on the ridges 64 of the hub 43 pressing into the relatively soft interior of plastic extractor hub 42.

The technique of using plunger assembly 12 to withdraw needle 16 has the advantage of providing an additional measure of safety, in that the needle is immediately retracted directly into a safe position. On the other hand, the technique of withdrawing the needle by pulling on cylinder 14 may be easier to perform, since it is fully consistent with conventional syringes and the medical personnel do not have to change the way in which syringe 10 is traditionally used. In the latter traditional case, needle 16 is drawn into barrel 14 after it is fully removed from the patient, as explained above.

The method of attachment between extractor 26 and needle 16 offers an advantage in simplicity of use over the methods of, for example, U.S. Pat. Nos. 4,675,005 to DeLuccia, 4,747,830 to Gloyer et al, 4,919,652 to Alter et al, and 4,986,813 to Blake III et al, which require the rotation of the plunger after medication is dispensed, to disengage the needle from the syringe barrel and to engage it to the plunger.

As shown in FIG. 6, after plunger assembly 12 has been completed withdrawn to its initial position as seen in FIG. 2, needle 16 is completely enclosed within barrel 14. As the tip 21a of needle 16 clears the proximal end of opening 50, the clamping action of elastomeric piston 28 on flange 31 of extractor 26 tends to bring proximal end surface 40 of flange 31 into contact with distal end flange 30 of slider 22, thereby rotating needle 16 transversely, to point toward a side of barrel 14. If plunger assembly 12 is subsequently pushed inward, into barrel 14, tip 21a of needle 16 will dig into funnel shaped surface 54 of barrel 14, preventing its later exposure or reuse. Needle 16 is thus totally enclosed in a manner permitting its safe handling and disposal.

Figure 7:
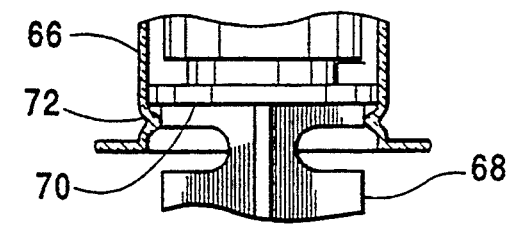
FIG. 7 is a fractional longitudinal cross-sectional elevation of a proximal portion of a barrel of a conventional hypodermic syringe, showing a plunger of the syringe pulled outward against a ring used to prevent inadvertent removal of the plunger from the barrel.
Figure 8:
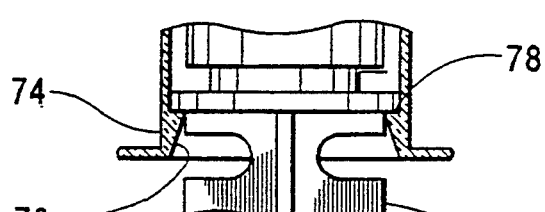
FIG. 8 is a cross-sectional elevation similar to FIG. 7, showing an improved form of the ring of FIG. 7.

A further refinement in preventing the surreptitious disassembly of the syringe by a drug abuser after disposal may be employed, as best understood by examining the differences between FIGS. 7 and 8. FIG. 7 shows a cross-sectional view of the proximal portion 66 of a conventional syringe, with a conventional plunger 68 pulled outward, so that a flange 70 of plunger 68 rests against an inwardly extending ring 72. While this arrangement is adequate to prevent inadvertent removal of plunger 68 from the syringe, it is not difficult for a drug abuser to remove the plunger. In the structure shown in FIG. 8, on the other hand, an improved ring 74 may alternately be provided, with a slanted surface 76 facilitating the insertion of plunger 68, as required in the assembly of the syringe, while a relatively flat annular surface 78 prevents removal of the plunger after disposal of the syringe. In this way, it is made particularly difficult for a drug abuser to remove the plunger to gain access to a needle held within cylindrical surface 37. Thus, the surreptitious disassembly and reassembly of the syringe may be prevented.

Figure 9:
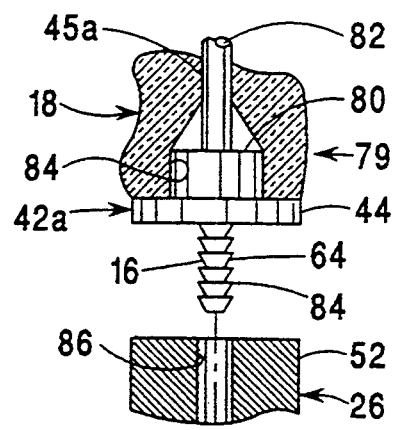
FIG. 9 is a fractional longitudinal elevation of an alternate structure for gripping a needle for retraction, showing a proximal portion of a needle within a Luer coupling, together with a distal tip of a needle extractor.

An alternative structure for attaching needle 16 to extractor 26 is shown in FIG. 9, with like numerals being used to designate parts with like functions. In the FIG. 9 structure, needle subassembly 79 is formed when a collar 42a, including a needle hub 80 and a needle flange 44, is attached to a needle 16, preferably using a swaging process, between a distal needle portion 82 and a relatively short proximal needle portion 84. Needle hub 80 is directed toward distal needle portion 82. Luer hub 18 includes an enlarged cavity 84, into which needle hub 82 extends when distal needle portion 82 is fully inserted through needle receiving hole 45a. An abutting surface 45 of Luer hub 18 transmits thrust forces to a distal side of needle flange 44 when needle 16 is withdrawn from a patient. Proximal needle portion 84 may include a series of ridges 64 to increase the force which can be applied by extractor 26 to extract needle 16. Hole 86 within tip portion 52 mates with proximal needle portion 84.

While the invention has been described in its preferred forms or embodiments with some degree of particularity, it is to be understood that this description has been given only by way of example and that numerous changes in the details of construction, fabrication and use, including the combination and arrangement of parts, may be made without departing from the spirit and scope of the invention.

What is claimed is:

1. A hypodermic syringe comprising:

a barrel having a generally cylindrical cavity extending inward from a proximal end thereof and a needle attachment coupling at a distal end thereof, said needle attachment coupling including an attachment portion, a coupling opening extending therethrough from said generally cylindrical cavity, and a releasable abutment portion;

a needle hub including a mating portion attached to said attachment portion of said needle attachment coupling, a proximal abutment surface, and a needle receiving hole extending therethrough from said proximal abutment surface to a distal end of said hub;

a needle subassembly including a needle with a distal point and with a hole extending axially through said needle, and a needle flange mounted between a distal portion of said needle and a proximal portion of said needle subassembly, with said proximal portion of said needle subassembly extending into said coupling opening, and with said needle flange extending outward between said proximal abutment surface of said needle attachment hub and said releasable abutment portion of said needle attachment coupling; and a plunger mounted to slide within said generally cylindrical cavity, including a slide extending outward from said generally cylindrical cavity, a piston forming a sealing engagement with said generally cylindrical cavity, and a needle extractor extending from a distal end of said plunger, said needle extractor including gripping means for engaging said proximal portion of said needle subassembly when said plunger is moved to a distal end of said generally cylindrical cavity, said needle extractor including release means for moving said releasable abutment from a blocking configuration, in which motion of said needle flange past said releasable abutment is prevented, to a released configuration, in which motion of said needle flange past said releasable abutment is permitted;

wherein said releasable abutment includes a plurality of segments arranged around said coupling opening, forming a restriction of said coupling opening to prevent passage therethrough of said needle flange;

wherein a distal extractor tip of said needle extractor includes a tubular portion having an inner surface forming said gripping means, and an outer surface forming said release means by deflecting said segments outward to permit passage of said needle flange through said coupling opening;

wherein said plunger includes elastic means for holding said distal extractor tip disposed at an acute angle relative to a central axis of said generally cylindrical cavity;

wherein said generally cylindrical cavity is of sufficient length to enclose said needle subassembly when said proximal end of said needle subassembly is held by said gripping means;

wherein said generally cylindrical cavity includes, at a distal end, a funnel shaped surface extending inward to said coupling opening;

wherein said needle extractor includes a proximal extractor surface opposite said distal extractor tip, said proximal extractor surface being inclined relative to an axis of said distal tip;

wherein said plunger includes a plunger surface extending perpendicularly to said central axis of said generally cylindrical cavity;

wherein said elastic means holds said proximal extractor surface against said plunger surface;

wherein said needle extractor further includes an extractor hub portion and an extractor flange portion, said extractor hub portion extending between said distal extractor tip and said extractor flange portion, said proximal extractor surface being formed as part of said extractor flange portion; and wherein said piston includes an elastic distal piston portion extending around said extractor flange portion, with said extractor hub portion extending through an aperture in said distal piston portion, with said distal piston portion holding said proximal extractor surface against said plunger surface.

2. A hypodermic syringe comprising:

a barrel having a generally cylindrical cavity extending inward from a proximal end thereof and a needle attachment coupling at a distal end thereof, said needle attachment coupling including an attachment portion, a coupling opening extending therethrough from said generally cylindrical cavity, and a releasable abutment portion;

a needle hub including a mating portion attached to said attachment portion of said needle attachment coupling, a proximal abutment surface, and a needle receiving hole extending therethrough from said proximal abutment surface to a distal end of said hub;

a needle subassembly including a needle with a distal point and with a hole extending axially through said needle, and a needle flange mounted between a distal portion of said needle and a proximal portion of said needle subassembly, with said proximal portion of said needle subassembly extending into said coupling opening, and with said needle flange extending outward between said proximal abutment surface of said needle attachment hub and said releasable abutment portion of said needle attachment coupling; and a plunger mounted to slide within said generally cylindrical cavity, including a slide extending outward from said generally cylindrical cavity, a piston forming a sealing engagement with said generally cylindrical cavity, and a needle extractor extending from a distal end of said plunger, said needle extractor including gripping means for engaging said proximal portion of said needle subassembly when said plunger is moved to a distal end of said generally cylindrical cavity, said needle extractor including release means for moving said releasable abutment from a blocking configuration, in which motion of said needle flange past said releasable abutment is prevented, to a released configuration, in which motion of said needle flange past said releasable abutment is permitted.

3. The hypodermic syringe of claim 2:

wherein said releasable abutment includes a plurality of segments arranged around said coupling opening, forming a restriction of said coupling opening to prevent passage therethrough of said needle flange; and wherein a distal extractor tip of said needle extractor includes a tubular portion having an inner surface forming said gripping means, and an outer surface forming said release means by deflecting said segments outward to permit passage of said needle flange through said coupling opening.

4. The hypodermic syringe of claim 3:

wherein said segments are formed as integral portions of said barrel;

wherein said segments are separated by slots extending inward from distal surfaces of said segments, in a longitudinal direction along said barrel; and wherein said segments are formed to block passage of said needle flange in an undeflected state.

5. The hypodermic syringe of claim 3:

wherein said plunger includes elastic means for holding said distal extractor tip disposed at an acute angle relative to central axis of said generally cylindrical cavity;

wherein said generally cylindrical cavity is of sufficient length to enclose said needle subassembly when said proximal end of said needle subassembly is held by said gripping means; and wherein said generally cylindrical cavity includes, at a distal end, a funnel shaped surface extending inward to said coupling opening.

6. The hypodermic syringe of claim 5:

wherein said needle extractor includes a proximal extractor surface opposite said distal extractor tip, said proximal extractor surface being inclined relative to an axis of said distal tip;

wherein said plunger includes a plunger surface extending perpendicularly to said central axis of said generally cylindrical cavity; and wherein said elastic means holds said proximal extractor surface against said plunger surface.

7. The hypodermic syringe of claim 2:

wherein said needle flange is formed as part of a collar secured in place on said needle;

wherein a hub extending from a proximal side of said needle flange is additionally part of said collar, said hub forming said proximal portion of said needle assembly.

8. The hypodermic syringe of claim 2:

wherein said needle flange is formed as part of a collar secured in place on said needle, with a distal portion of said needle extending from a distal side of said collar, and with a proximal portion of said needle extending from a proximal side of said collar, said proximal portion of said needle forming said proximal portion of said needle assembly; and wherein a hub extending from a distal side of said needle flange is additionally part of said collar.

9. The hypodermic syringe of claim 2 wherein said proximal portion of said needle subassembly includes a ridge formed to resist slippage when a tensile force is applied to said proximal portion of said needle.

10. The hypodermic syringe of claim 2 wherein a sealant is applied within an annular space between said needle and said needle hub.

11. The hypodermic syringe of claim 2:
wherein said attachment portion of said needle attachment coupling and said mating portion of said needle hub are engageable by relative rotation in a first direction and disengageable by relative rotation in a direction opposite said first direction; and
wherein said needle and said needle hub are together attachable and removable from a distal end of said needle attachment coupling, from outside said barrel.

12. The hypodermic syringe of claim 2, additionally includes plunger travel limiting means for stopping outward motion of said plunger beyond said distal end of said barrel.

13. A hypodermic syringe comprising:
a needle subassembly including a needle and an outward extending needle flange, said needle having a distal point, a distal needle portion extending to said distal point from said needle flange, and a longitudinal hole extending through said needle, said needle subassembly including a proximal needle subassembly portion extending from said needle flange to a proximal end of said needle subassembly;
a barrel having a distal barrel end and a proximal barrel end, including a generally cylindrical cavity extending inward from said proximal barrel end, a distal barrel opening extending outward between said generally cylindrical cavity and said distal barrel end, and fastening means surrounding said distal barrel opening;
needle mounting means for removably mounting said needle subassembly at said distal barrel end, said needle mounting means including a needle receiving hole through which said distal needle portion extends and projects, a first abutment surface at a proximal end of said needle receiving hole, extending outward therefrom adjacent a distal side of said needle flange to prevent movement of said needle outward through said needle receiving hole, and engagement means releasably engaging said fastening means;
releasable needle holding means, including a second abutment surface extending adjacent a proximal side of said needle flange, to prevent movement of said needle subassembly through said distal barrel opening into said generally cylindrical cavity;
a plunger mounted to slide within said generally cylindrical cavity between a fully extended position, in which a distal plunger portion of said plunger is held adjacently within said proximal barrel end, and a fully inserted position, in which said distal plunger position is inwardly adjacent to said distal barrel end, said plunger having sealing means to maintain a fluid tight seal between said distal plunger end and said generally cylindrical cavity;
gripper means, attached to said distal plunger end, for engaging said proximal needle subassembly portion when said plunger is in said fully inserted position; and
release means for releasing said releasable needle holding means, when said plunger is in said fully inserted position, thereby permitting movement of said needle subassembly through said distal barrel opening into said generally cylindrical cavity as said plunger is subsequently moved from said fully inserted position to said fully extended position.

14. The hypodermic syringe of claim 13:
wherein said gripper means includes an internal surface of a tubular tip, extending at said plunger distal end, movable into said distal barrel opening as said plunger is moved into said fully inserted position;
wherein said releasable needle holding means includes a plurality of segments arranged around said distal barrel opening forming a diametral restriction of said distal barrel opening; and
wherein said release means includes an external surface of said tubular tip.

15. The hypodermic syringe of claim 14 wherein said segments have integral portions of said barrel separated by slots extending longitudinally from said second abutment surface.

16. The hypodermic syringe of claim 13:
wherein said plunger further includes elastic means for holding said gripper means directed at an acute angle with respect to a central axis of said generally cylindrical cavity, so that a needle held by said gripper means, with said plunger in said fully extended position, is directed toward an outer wall of said generally cylindrical cavity; and
wherein a distal end of said generally cylindrical cavity includes a funnel shaped surface directing said gripper means and said release means into said distal barrel opening as said plunger is moved into said fully inserted position.

17. A hypodermic syringe comprising:
a container for ejecting fluid having an internal cavity between a fluid ejecting end thereof and a proximal end thereof and a piston assembly having a seal end movable from said proximal end to said fluid ejecting end to eject fluid and retractable towards said proximal end;
a needle attachment assembly affixed to said fluid ejecting end of said container, said needle attachment assembly having a hollow first column with an opening extending therethrough in fluid communication with said cavity, said column being tapered inward at a distal end thereof and having a plurality of slits from said distal end thereof towards said container separating a plurality of segments at said distal end;
a needle subassembly including a needle with hole extending axially therethrough, a needle flange affixed remote from one end of said needle, and a second hollow column extending from said flange towards said one end and sized to fit within said first column opening such that the end of said segments are juxtaposed to one surface of said flange, said needle subassembly further including means juxtaposed to the other side of said flange for holding said needle subassembly on said attachment assembly column; and
needle extractor means, including a third hollow column affixed to said seal end of said piston assembly, said third column being sized such that the exterior thereof enters said first column and separates said segments so that the ends thereof are spaced from said one surface of said flange, said third column further being sized such that the interior thereof grabs said second column, said needle assembly, including said flange being retracted through said first column upon retraction of said piston assembly.

18. The syringe according to claim 17 wherein said segments are biased inward.

19. The syringe according to claim 17 wherein one of said second column exterior surface or said third column interior surface has a non-smooth surface.

20. The syringe according to claim 19 wherein said non-smooth surface has ridges.

21. The syringe according to claim 19 wherein said segments are biased inward.

22. The syringe according to claim 21 wherein said first, second and third columns are hollow cylinders.

23. The syringe according to claim 17 wherein said first, second and third columns are hollow cylinders.

24. A syringe comprising:
a barrel including a luer tip,
a needle assembly detachably mounted on said luer tip, said needle assembly including a hub receiving said luer tip and a needle slidably positioned within said hub, said needle having a flange mounted thereon and said flange being captured between said hub and said luer tip to immobilize said needle.

25. The syringe of claim 24, further comprising:
said luer tip including a coupling opening extending therethrough and the distal end of said luer tip being expandable from a constricted position wherein at least a distal portion of the coupling opening is smaller than said needle flange to an expanded position wherein the coupling opening is larger than said needle flange.

26. The syringe of claim 25, further comprising:
an extractor moveable within said barrel, said extractor including at a distal end thereof a needle coupling to connect said needle to said extractor and a release face to expand said luer tip of said barrel.

27. The syringe of claim 26, further comprising:
the expandable distal end portion of said luer tip being segmented.

28. The syringe of claim 25, further comprising:
an extractor moveable within said barrel, a distal tip of said extractor having a release face smaller in diameter than said coupling opening and larger in diameter than said flange and a needle coupling at a distal end of said extractor to connect said needle to said extractor.

29. The syringe of claim 28, further comprising:
said needle coupling being disposed on said extractor with respect to said release face such that when said needle is coupled to said extractor, said needle flange
is sufficiently proximate said release face that said expandable distal tip will not engage said flange as said needle is withdrawn through the coupling opening.

30. The syringe of claim 29, further comprising:
the expandable distal end portion of said luer tip being segmented.

31. A syringe and detachable needle assembly combination comprising:
a barrel including a luer tip,
a needle assembly detachably mounted on said luer tip, said needle assembly including a hub receiving said luer tip and a needle slidably positioned within said hub, said needle having a flange mounted thereon and said flange being captured between said hub and said luer tip to immobilize said needle.

32. The syringe and needle assembly combination of claim 31, further comprising:
said luer tip including a coupling opening extending therethrough and the distal end of said luer tip being expandable from a constricted position wherein at least a distal portion of the coupling opening is smaller than said needle flange to an expanded position wherein the coupling opening is larger than said needle flange.

33. The syringe and needle assembly combination of claim 32, further comprising:
an extractor moveable within said barrel, said extractor including at a distal end thereof a needle coupling to connect said needle to said extractor and a release face to expand said luer tip of said barrel.

34. A syringe and detachable needle assembly combination comprising:
a barrel including a luer tip, a coupling opening extending to a radially expandable distal tip of said luer tip and an internally threaded locking skirt around said luer tip,
a needle assembly including a hub and a needle, said hub including a distal end, an open proximal end receiving said luer tip and locking ears extending outwardly from said hub to engage said internal threads of said locking skirt to detachably lock said hub to said barrel, and said needle having a flange mounted thereon, said needle being slidably positioned through the distal end of said hub with said flange being captured between said hub and said luer tip to immobilize said needle against axial movement.

35. The syringe and needle assembly combination of claim 34, further comprising:
said expandable tip of said luer tip having a constricted position wherein the diameter of the coupling opening is smaller than the diameter of said flange and an expanded position wherein the diameter of the coupling opening is larger than the diameter of said flange,
an extractor moveable within said barrel, said extractor including at a distal end thereof a needle coupling to connect said needle to said extractor and a release face to expand said luer tip of said barrel to said expanded position when said needle is coupled to said extractor.

36. A needle assembly for use with a medical device having a luer tip for sealable, detachable connection to such needle assembly, comprising:
a hub including a needle passage extending from a distal end thereof and a luer tip passage extending from a proximal end thereof, said hub having a proximal abutment surface within the luer tip passage;
a needle including a flange, said needle being slidably positioned through the needle passage of said hub with said flange abutted against said proximal abutment surface of said hub.

37. The needle assembly of claim 36 further comprising:

said needle having a coupling thereon for connection to an extractor of a medical device adapted to pull said needle from the needle passage of said hub.

38. The needle assembly of claim 36 further comprising:
said hub including ears thereon configured to releasably engage a medical device.

39. The needle assembly of claim 36 further comprising:
the luer tip passage of said hub including a female luer taper.

40. The needle assembly of claim 36 further comprising:
the luer tip passage of said hub being configured to position said flange between said abutment of said hub and the distal end of the luer tip of a medical device to which said needle assembly can be attached.

41. The needle assembly of claim 36 further comprising:
said abutment of said hub being positioned in the luer tip passage of said hub such that when said needle assembly is connected to the luer tip of a medical device, said flange is captured between said abutment of said hub and the distal end of the luer tip of such medical device.

42. The needle assembly of claim 36 further comprising:
sealant within at least a portion of the needle passage of said hub about said needle.

43. A needle assembly for use with a syringe having a luer tip and an internally threaded locking skirt around the luer tip for sealable, detachable locked connection of such needle assembly to such medical device, comprising:
a hub including locking ears on the outside of said hub configured to engage the internal threads of the locking skirt of a medical device to which said hub may be connected, a needle passage axially extending from a distal end of said hub, a luer tip passage axially extending from a proximal end of said hub configured to receive the luer tip of such medical device, and a proximally facing abutment surface at the distal end of the luer tip passage;
a needle including a flange, said needle being slidably positioned through the needle passage of said hub with said flange abutted against said abutment surface of said hub.

44. The needle assembly of claim 43 further comprising:
said needle having a coupling thereon for connection to an extractor of a medical device adapted to pull said needle from the needle passage of said hub.

45. The need assembly of claim 43 further comprising:
the luer tip passage of said hub including a female luer taper.

46. The needle assembly of claim 43 further comprising:
the luer tip passage of said hub being configured to position said flange between said abutment of said hub and the distal end of the luer tip of a medical device to which said needle assembly may be attached.

47. The needle assembly of claim 43 further comprising:
said abutment surface of said hub being positioned in the luer tip passage of said hub such that when said needle assembly is connected to the luer tip of a medical device, said flange is captured between said abutment of said hub and the distal end of the luer tip of such medical device.

48. The needle assembly of claim 43 further comprising:
sealant within at least a portion of the needle passage of said hub about said needle.

49. A needle assembly for use with a syringe having a luer tip, an internally threaded locking skirt around the luer tip for sealable, detachable locked connection of such needle assembly to such medical device and a plunger having an extractor thereon for retracting a needle into the medical device from the barrel, comprising:
a hub including locking ears on the outside of said hub configured to engage the internal threads of the locking skirt of a medical device to which said hub may be connected, a needle passage axially extending from a distal end of said hub, a luer tip passage axially extending from a proximal end of said hub configured to receive the luer tip of such medical device, and a proximally facing abutment surface at the distal end of the luer tip passage;
a needle including a flange, said needle being slidably positioned through the needle passage of said hub with said flange abutted against said abutment surface of said hub, said abutment surface being spaced from the proximal end of said hub to abut said flange against the distal end of the luer tip of a syringe that may be connected to said needle assembly.

50. The needle assembly of claim 49 further comprising:
said needle having a coupling thereon for connection to an extractor of a medical device that may be connected to said needle assembly.

51. The needle assembly of claim 49 further comprising:
sealant within at least a portion of the needle passage of said hub about said needle.

52. A syringe comprising:
a barrel having a hollow interior and a male luer tip at a distal end of said barrel,
said luer tip including a coupling opening extending therethrough and a distal end of said luer tip being expandable from a constricted position wherein at least a distal portion of the coupling opening is smaller than a desired size to an expanded position wherein the coupling opening is larger than the desired size.

53. The syringe of claim 52, further comprising:
the expandable distal end portion of said luer tip being segmented.

54. The syringe of claim 52, further comprising:
an extractor moveable within said barrel, a distal tip of said extractor having a release face smaller in diameter than said coupling opening in the expanded position of said luer tip and larger in diameter than said coupling opening in the constricted position to said luer tip.

55. A syringe for use with a needle assembly having a hub and a needle slidably removable from the hub, comprising:
a barrel having a hollow interior and a male luer tip at a distal end of said barrel,
said luer tip including a coupling opening extending therethrough and a distal end of said luer tip being expandable from a constricted position wherein at least a distal portion of the coupling opening is smaller than a portion of a needle attached to said barrel to an expanded position wherein the coupling opening is larger than a needle attached to said barrel.

56. The syringe of claim 55, further comprising:

an extractor moveable within said barrel, said extractor including at a distal end thereof a release face to expand said luer tip of said barrel.

57. The syringe of claim 55, further comprising:

the expandable distal end portion of said luer tip being segmented.

58. The syringe of claim 55, further comprising:

an extractor moveable within said barrel, a distal tip of said extractor having a release face smaller in diameter than said coupling opening and larger in diameter than any portion of the needle that is removable from the hub of a needle assembly mounted on said barrel, and said extractor having a needle coupling at a distal end thereof to connect said needle to said extractor.

59. The syringe of claim 58, further comprising:

said needle coupling being disposed on said extractor with respect to said release face such that when a needle is coupled to said extractor, a portion of such needle that is larger than the coupling opening when said luer tip is in the constricted position is sufficiently proximate said release face that said expandable distal luer tip will not engage any removable portion of the needle as the needle is withdrawn through the coupling opening.

60. The syringe of claim 59, further comprising:

the expandable distal end portion of said luer tip being segmented.

* * * * *